United States Patent [19]

Wirth

[11] Patent Number: 4,665,204

[45] Date of Patent: May 12, 1987

[54] DIESTER DERIVATIVES OF TOCOPHEROL

[75] Inventor: Ronald P. Wirth, Minneapolis, Minn.

[73] Assignee: Henkel Corporation, Ambler, Pa.

[21] Appl. No.: 749,958

[22] Filed: Jun. 27, 1985

[51] Int. Cl.$^4$ ............................................ C07D 311/72
[52] U.S. Cl. ..................................................... 549/410
[58] Field of Search ........................................... 549/410

[56] References Cited

U.S. PATENT DOCUMENTS 2,680,749  6/1954  Cawley et al. ...................... 549/410
2,875,195  2/1959  Humphlett et al. ................. 549/410
2,988,553  6/1961  Küssner et al. ..................... 549/410

FOREIGN PATENT DOCUMENTS 58-203982  11/1983  Japan .

Primary Examiner—Nicky Chan
Attorney, Agent, or Firm—Ernest G. Szoke; Patrick J. Span

[57] ABSTRACT

Tocopherol diester derivatives having high vitamin E potency can be produced by the esterification of tocopherol acid esters with amino alcohols. Some preferred tocopherol diesters also have excellent water solubility. One of the preferred diesters is the tocopherol diester having choline, a vitamin $B_4$ moiety.

11 Claims, No Drawings

DIESTER DERIVATIVES OF TOCOPHEROL

BACKGROUND OF THE INVENTION

Tocopherol compounds, also designated as vitamin E, are active components in vegetable oils. Vitamin E activity refers to the physiological activity of this group of nutrient materials. Materials having a vitamin E activity all belong to a distinct series of compounds which are all derivatives of chroman-6-ol. These compounds are all tocol derivatives having an isoprenoid $C_{16}$-sidechain. The term "tocol" is used to mean 2-methyl-2-(4',8,12'-trimethyltridecyl)chroman-6-ol. These compounds are alpha-, beta-, gamma-, and delta-tocopherol, and are of primary importance for vitamin E activity. Of these, alpha-tocopherol has the highest vitamin E activity and is the most valuable.

Such naturally occurring tocopherol homologues are generally isolated from natural products such as vegetable oil sources by various combinations of procedures such as esterification, saponification, extraction, distillation, ion exchange, adsorption chromotography, precipitation of sterols, and crystallization. The tocol concentrate isolated will vary depending on the particular separation technique used in addition to the vegetable source. One such concentrate, for example, contains mixtures of tocopherol with approximately 40% by weight residual sterols and hydrocarbons.

A well known commercial activity is the conversion of tocopherol, and especially d-alpha-tocopherol into a solid form for convenient human consumption. One of the best methods commercially used to solidify tocopherol is to prepare tocopherol succinate. Typically, tocopherol succinate is prepared by reacting tocopherol with succinic anhydride, and then isolating the half ester product by crystallization. References describing methods of this nature are described in U.S. Pat. No. 3,538,119 and in British Pat. No. 866,489. Another reference which describes both the preparation of alpha-tocopheryl succinate and its recovery is British Pat. No. 1,114,150.

For medicinal and health applications requiring tocopherol, solid tocopherol derivatives are prepared. It is desired that such tocopherol derivatives be capable of dissolving in an aqueous solution and be highly potent with a high degree of vitamin E biological activity per unit. The preparation of tocopherol derivatives is described in U.S. Pat. No. 2,680,749, which describes, as a preferred method, reacting tocopherol with a suitable polybasic acid anhydride such as succinic acid anhydride under usual esterification conditions. The tocopherol acid esters are then esterified with polyethylene glycol also in accordance with well known esterification techniques.

Vitamin E derivatives disclosed in the early disclosure No. 58-203982 for Application No. 57-87580, published by the Japanese Patent Bureau includes mono amino dicarboxylic acid derivatives of tocopherol. Such compounds, according to this reference are vitamin E derivatives formed with amino acids.

It is an object of the instant invention to provide a diester tocopherol derivative. In preferred aspects the instant invention provides tocopherol derivatives of high potency and of water solubility. Advantageously, in another preferred aspect the instant invention provides a water soluble tocopherol derivative of high potency wherein the compound includes the choline, vitamin $B_4$ unit. A further object of the instant invention is to provide water soluble tocopherol derivatives which can further be used in applications in the fields of: medication, foods, cosmetics, fisheries, and animal husbandry. Other objects will become apparent as this description proceeds.

BRIEF DESCRIPTION

Diester tocopherol derivatives are described herein. These derivatives can be represented by the formula:

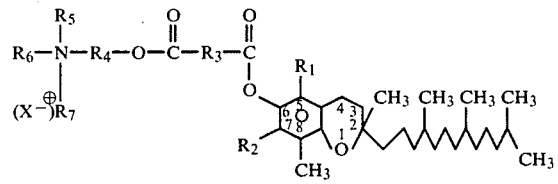

wherein:
(1) $R_1$ is a $CH_3$ or H,
(2) $R_2$ is a $CH_3$ or H,
(3) $R_3$ can be a saturated or unsaturated hydrocarbon residue from a dicarboxylic acid,
(4) $R_4$ can be a saturated or unsaturated hydrocarbon residue of an alcohol,
(5) $R_7$ must be a moiety selected from the group consisting of: hydrogen, a saturated hydrocarbon, and an unsaturated hydrocarbon, while $R_5$ and $R_6$ are saturated or unsaturated hydrocarbons, and
(6) $(X^-)$ is an anion.

To prepare the diester tocopherol derivatives of the instant invention the tocopherol feed material is first esterified with a dicarboxylic acid or dibasic acid anhydride to yield a tocopherol acid ester which is in turn reacted with a mono alcohol tertiary amine in another esterification reaction. After the formation of the tocopherol diester product, neutralization can be used to remove the catalyst. Thereafter, an appropriate acid is added, producing the stabilized tocopherol diester amine salt. Preferably, however, the product is subjected to another reaction converting the tertiary amine moiety to a quarternary ammonium salt, thereby producing the preferred diesters having greater stability and water solubility. When these embodiments are made, the anionic moiety of $(X^-)$ is determined by the quarternizing reagent used to convert the tertiary amine moiety to the quarternary ammonium salt.

DETAILED DESCRIPTION

This invention provides derivatives of any of the well known vitamin E active tocopherols including alpha-tocopherol, beta-tocopherol, gamma-tocopherol and delta-tocopherol, either in pure form or in mixtures of two or more of such tocopherols. Tocopherol concentrations can also be used which were derived from both natural and synthetic tocopherols. Suitable concentrations of natural tocopherol homologues can be obtained from such natural sources as soybean, peanut, cottonseed, palm, safflower, linseed, sunflower, rapeseed and from plant sources such as palm leaves, lettuce, alfalfa, rubber latex, and a variety of other plant materials. Preferred feed material is the tocopherol homologue having the highest vitamin E potency which is alpha-tocopherol.

Two esterification reactions are conducted in order to prepare diester tocopherol derivatives of the instant invention. The first esterification, producing tocopherol acid esters, can be conducted in accordance with any of the well known procedures for making the esters of hydroxylic compounds such as the method described in U.S. Pat. No. 3,538,119. A preferred method is to react tocopherol with a dibasic acid anhydride in an organic solvent such as toluene, or benzene in the presence of an esterification catalyst such as p-toluene sulfonic acid, oxalic acid, or hydrochloric acid at a suitable elevated temperature.

The dibasic acid used will determine the structure of $R_3$. The tocopherol acid esters which are suitable are the acid esters of any of the well known tocopherol homologues with dicarboxylic acids such as: succinic acid, citraconic acid, methylcitraconi a, ita acid, maleic acid, glutaconic acid fumaric acid or phthalic acid. Preferably the dicarboxylic acid used will result in $R_3$ having from one to six carbon atoms. When succinic acid is used, $R_3$ will have two carbon atoms. Dicarboxylic acid anhydrides suitable for preparing the diester tocopherol derivatives of the instant invention are commercially available.

The preparation of diester tocopherol derivatives embodying this invention is completed by esterifying any of the tocopherol acid esters with an alkanolamine. Suitable mono alkanol tertiary amines have the formula:

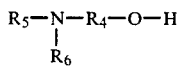

wherein $R_4$ can be saturated or unsaturated. Acceptably it can have from 1-10 carbon atoms; preferably, it has from 1-4 carbon atoms. $R_5$ and $R_6$ is a saturated or unsaturated hydrocarbon. Acceptably, these hydrocarbons have 1 to 10 carbon atoms, preferably they are saturated or unsaturated aliphatic hydrocarbons having from 1-3 carbon atoms.

Well known esterification techniques can also be used for the second esterification wherein the tocopherol acid ester product from the first esterification is esterified with the above indicated mono alkanolamine. Thus, the tocopherol acid esters can be esterified using a solvent such as benzene, toluene, hexane, heptane, and octane. Preferably, toluene is used which allows the water formed during the esterification to be removed by azeotropic distillation. The esterification is promoted by the inclusion in the reaction mixture of an esterification catalyst such as p-toluene sulfonic acid, benzene sulfonic, methane sulfonic, hydrochloric acid, sulfuric, hydrobromic and other well known acidic catalysts. Preferred acids are those which make highly soluble alkanol amine salts. Preferably, the reaction is conducted at elevated temperatures, most preferably at or near the azeotropic distillation point.

After the second esterification a base such as an alkali metal hydroxide or alkaline earth metal oxide such as calcium oxide can be added to neutralize the acid catalyst. The salt from this neutralization is then removed to leave the solution containing the diester tocopherol derivative. Most preferably, calcium oxide is used to neutralize the acid catalyst since the neutralization salt can then be removed by filtration.

The solvent used in esterification should be removed, and a suitable acid added to the diester tocopherol product in a sufficient amount to completely neutralize the diester and introduce the anion forming the tertiary amine salt of the diester tocopherol derivative. Suitably, the acid used can be selected from the group consisting of: hydrochloric, hydrobromic, hydroiodic, hydrofluoric, sulfuric; also suitable are organic acids such as: acetic, tartaric, citric, lactic, glylolic, and ascorbic acid. These organic acids are used to produce the tertiary amine salts; in this case $(X^-)$ will be the organic, anionic moiety of these acids, and $R_7$ is hydrogen.

Preferably, however, after the removal of the solvent used in the second esterification, the tertiary amine portion of the diester tocopherol derivative is reacted with a quarternizing reagent to convert the tertiary amine portion to the neutral quarternary ammonium salt. A "quarternizing reagent" is a compound capable of reacting with a tertiary amine to convert it to a tetra substituted ammonium salt, also known as a quarternary ammonium salt. Such quarternizing reagents are well known, and are frequently called alkylating agents, although as pointed out in Kirk-Othmer *Encyclopedia of Chemical Technology*, the hydrocarbon radicals capable of converting a tertiary amine to a quarternary ammonium salt can be "substituted or unsubstituted, saturated or unsaturated, aliphatic or aromatic, and have branched or normal chains."

Quarternizing reagents which can be used to convert the tocopherol diesters tertiary amine moiety to a quarternary ammonium salt have both an anionic portion and a hydrocarbon portion which can be aliphatic or aromatic, saturated or unsaturated and branched or linear. These quarternary reagents will therefore give the preferred embodiments of the instant invention wherein $R_5$, $R_6$, and $R_7$ are all saturated or unsaturated hydrocarbons; acceptably having from 1-10 carbon atoms. In this case and $(X^-)$ is the anionic moiety from the quarternizing reagent. Representative but non exhaustive quarternizing reagents which can be used are:

(1) saturated or unsaturated hydrocarbon halides acceptably having from 1 to 10 carbon atoms; preferably the quarternizing reagent is an alkyl halide most preferably having from 1 to 3 carbon atoms, with methyl halide being the most preferred due to high potency and water solubility;

(2) a hydrocarbon sulfate, preferably dimethyl sulfate;

(3) a hydrocarbon sulfonate; the sulfonate portion being: $RSO_3$ wherein R is acceptably selected from the group consisting of: $CF_3$, benzene, and p-toluene, and with the hydrocarbon portion being a saturated or unsaturated hydrocarbon having from 1-10 carbon atoms; preferably it is an alkyl group having from 1-3 carbon atoms. Most preferably, the hydrocarbon sulfonate quarternizing reagent is selected from the group consisting of: methyl benzene sulfonate, methyl para toluene sulfonate, and methyl trifluoromethyl sulfonate.

If a hydrocarbon sulfate is used $(X^-)$ will be the anion of: $RSO_4$ where R can be a saturated or unsaturated aliphatic hydrocarbon; acceptably, it can have from 1-10 carbon atoms and preferably it is aliphatic; more preferably it is an alkyl group having from 1-3 carbon atoms and most preferably it is a methyl group.

When the preferred quarternizing reagents methyl or ethyl halide is used, and $R_4$ is the preferred 1-4 carbon atoms; and with $R_5$, $R_6$ and $R_7$ being from 1-3 carbon atoms, the diester tocopherol derivative will have better water solubility. When methyl halide is used, a methyl group is introduced. The tocopherol diester wherein $R_4$ has two carbon atoms, and $R_5$, $R_6$ and $R_7$ are all methyl groups has greater versatility, and is preferred, since this portion of the molecule is the structure of choline, or vitamin $B_4$.

A preferred method for the conversion of the tertiary amine portion of the tocopherol diester to the quarternary ammonium salt is by reacting the appropriate hydrocarbon halide, sulfate or sulfonate, with the tertiary amine diester tocopherol derivative in a polar solvent acceptably at temperatures in the range of from about 20° to about 120° C.; preferably in the range of from about 50° to about 75° C. Suitable polar solvents which may be used are alcohols, nitriles and toluene. Catalysts such as iodide salts can suitably be used for this reaction. Preferred examples are sodium iodide and tetra alkyl ammonium iodide. After the reaction has proceeded for a sufficient length of time, the neutral tocopherol diester ammonium salt will have been formed.

The process of the instant invention will be more fully understood from the examples which follow. These examples are intended to clarify and demonstrate the instant invention and not to limit it. All parts and percentages are by weight unless otherwise specified.

EXAMPLE I

PART A

A tocopherol acid monoester which can be used to prepare the diester derivatives of tocopherol can be prepared by conducting an esterification with a suitable amount of alpha-tocopherol and an equivalent of succinic acid anhydride. Suitably, an esterification catalyst such as p-toluene sulfonic acid monohydrate is used in an amount of about 1.2 equivalents. Toluene can be used as a preferred solvent. The reaction can be conducted at approximately 90°. At the conclusion of the reaction, the alpha-tocopherol succinate can be collected by crystallization. This product can then be subjected to a second esterification reaction as described in Part B of this example in order to produce the diester tocopherol derivatives of the instant invention.

PART B

Alpha-tocopherol succinate can be prepared by a method as described in Part A or can be obtained commercially and then used as hereinafter described to produce the diester tocopherol derivatives herein described.

Alpha-tocopherol succinate (6.0 parts) and N,N-dimethyl-aminoethanol (1.0 part) were condensed in toluene (6.4 parts) using p-toluenesulfonic acid monohydrate (2.6 parts) as a catalyst. The condensation was conducted at the boiling point of the mixture for a period of approximately 4 hours. The water of reaction was removed as the toluene-water azeotrope. The mixture was cooled, the catalyst was neutralized with calcium oxide (at greater than 2.5 equivalents) and the neutralization product was removed by filtration. The toluene solvent was removed by vacuum distillation to give a viscous brown oil. The alpha-tocopheryl N,Ndimethylaminoethyl succinate structure was confirmed by spectroscopic methods.

The product (1.0 part) was combined with iodomethane (1.1 parts) and acetonitrile (19.7 parts) and the mixture was heated at the boiling point for a period of approximately 1 hour under ambient pressure. After the reaction was complete, the solvent was removed by vacuum distillation to give a yellow waxy solid. The alpha-tocopheryl 2-(trimethyammonium)ethyl succinate, iodide salt structure was confirmed by spectroscopic methods.

The product has a theoretical potency of 864 IU/g and is soluble in water to an extent of approximately 5%.

What is claimed is:

1. A compound having the formula:

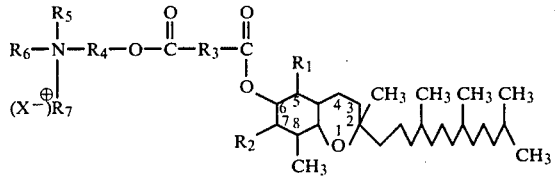

wherein:
(1) $R_1$ is a $CH_3$ or H,
(2) $R_2$ is a $CH_3$ or H,
(3) $R_3$ is the saturated hydrocarbon residue from a dicarboxylic acid,
(4) $R_4$ is the saturated or unsaturated hydrocarbon residue from the alcohol portion of an amino alcohol.
(5) $R_7$ must be a moiety selected from the group consisting of hydrogen, a saturated hydrocarbon, and an unsaturated hydrocarbon, while $R_5$ and $R_6$ are selected from the group consisting of: a saturated hydrocarbon, and unsaturated hydrocarbon, and
(6) $(X^-)$ an anion.

2. A compound as described in claim 1 wherein $R_3$ has from 1 to 6 carbon atoms; $R_4$ has from 1 to 10 carbon atoms; and wherein the saturated or unsaturated hydrocarbon from which $R_5$, $R_6$ and $R_7$ can be selected, has from 1 to 10 carbon atoms.

3. A compound having the formula:

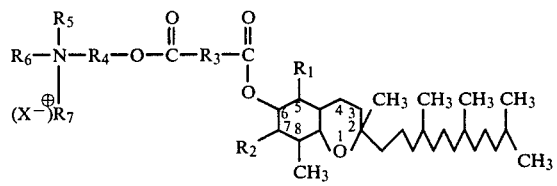

wherein:
(1) $R_1$ is a $CH_3$ or H,
(2) $R_2$ is a $CH_3$ or H,
(3) $R_3$ is the saturated hydrocarbon residue of a dicarboxylic acid wherein said residue contains 1–6 carbon atoms,
(4) $R_4$ is the saturated hydrocarbon reside of a monoalkanol tertiary amine and contains 1–10 carbon atoms,
(5) $R_7$ is hydrogen or a saturated aliphatic hydrocarbon group having 1–3 carbon atoms and $R_5$ and $R_6$ are a saturated aliphatic hydrocarbon having 1–3 carbon atoms, and
(6) $(X^-)$ is an anion.

4. A compound as described in claim 3 wherein $R_5$, $R_6$ and $R_7$ are all alkyl groups having from 1 to 3 carbon atoms, and wherein $(X^-)$ is an anionic moiety of a member selected from the group consisting of: a halide, a sulfate, and a sulfonate.

5. A compound as described in claim 4 wherein $R_5$, $R_6$, and $R_7$ are methyl groups 6. A compound as described in claim 5 wherein $R_4$ has two carbon atoms.

7. A compound as described in claim 5 wherein $R_3$ is from an acid selected from the group consisting of: succinic acid, citraconic acid, methyl citraconic acid, itaconic acid, maleic acid, fumaric acid, glutaconic acid and phthalic acid.

8. A compound as described in claim 6 wherein $R_1$ and $R_2$ are methyl groups.

9. A compound as defined in claim 3 wherein $R_4$ contains 1–4 carbon atoms.

10. A compound as defined in claim 9 wherein $(X^-)$ is an anionic moiety of an acid selected from the group consisting of hydrochloric, hydrobromic, hydroiodic, hydrofluoric, sulfuric, acetic, tartaric, citric, lactic, glycolic, and ascorbic acid.

11. α-Tocopheryl 2-(trimethylammonium) ethyl succinate iodide salt.

* * * * *